US00PP12407P2

(12) United States Plant Patent
Utecht

(10) Patent No.: US PP12,407 P2
(45) Date of Patent: Feb. 12, 2002

(54) GERANIUM PLANT NAMED 'FISROCCO'

(75) Inventor: Angelika Utecht, Montabaur (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/772,936

(22) Filed: Jan. 31, 2001

(51) Int. Cl.[7] ..... A01H 5/00
(52) U.S. Cl. ..... Plt./332
(58) Field of Search ..... Plt./332, 324

(56) References Cited

U.S. PATENT DOCUMENTS

PP9,353 P * 10/1995 Hanes ..... Plt./332

OTHER PUBLICATIONS

GTITM VPOVROM Citation for 'Fisrocco' as per QZ PBR 991043; Jul. 20, 1999.*
Official Gazette of the Community Plant Varity Office, Dec. 15, 1999, European Community Application.
German Application and Denomination, Dec. 15, 1998.
Fischer—Schmüllung Plant Alliance Catalogue, featuring 'Fisrocco' on p. 29, Germany, 2001.
Canadian application, denomination, Plant Varieties Journal No. 38, Jan. 2001, Canada. pp. 61–62.

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrocco', as described and illustrated, and particularly characterized by the combined features of purple-pink semi-double to double flowers, numerous, medium-sized inflorescence, and fresh-green, distinctly zoned foliage, medium tall, bushy plant habit.

1 Drawing Sheet

BACKGROUND OF THE INVENTION

The present invention comprises a new and distinct cultivar of geranium, botanically known as *Pelargonium peltatum*, and hereinafter referred to by the cultivar name 'Fisrocco'.

'Fisrocco' is a product of a planned breeding program which had the objective of creating new ivy geranium varieties with intense violet flower color and good cultivation ability. 'Fisrocco' originated from a hybridization made by the inventor Angelika Utecht in a controlled breeding program in Galar, Gran Canaria, Spain, in 1995.

The female parent was a hybrid seedling, No. 323-1(unpatented), derived from a cross between 'Guishiva', U.S. Plant Pat. No. 9,351, red-flowered, and 'Fisam', U.S. Plant Pat. No. 8,327, with light violet flowers, and (the seedling) characterized by red, double flowers, medium-green, zoned foliage, and medium tall, bushy plant habit. The male parent of 'Fisrocco', seedling no. 300-2 (unpatented), was derived from self-pollinating 'Fisrain', U.S. Plant Pat. No. 9,533, which had violet, single-type flowers, medium green foliage with relatively strong zonation and compact plant habit. 'Fisrocco' was selected as one flowering plant within the progeny of the stated cross by Angelika Utecht in 1996 in a controlled environment in Galdar, Gran Canaria, Spain. The first act of asexual reproduction of 'Fisrocco' was accomplished when vegetative cuttings were taken from the initial selection in the fall of 1996 in a controlled environment in Caldar, Gran Canaria, Spain, by, or under the supervision of, Angelika Utecht. Horticultural examination of plants grown from cuttings of the plant initiated in May 1997 in Hillscheid, Germany, and continuing thereafter, has demonstrated that the combination of characteristics as herein disclosed for 'Fisrocco' are firmly fixed and are retained through successive generations of asexual reproduction.

'Fisrocco' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisrocco', which in combination distinguish this geranium as a new and distinct cultivar:

1. purple-pink colored, semi-double to double flowers;
2. medium-sized, roughly semi-spherically shaped umbels;
3. light medium green, distinctly zoned, retatively small foliage;
4. early to medium spring flowering response, and rich flowering throughout the summer; and
5. medium tall, bushy and round plant habit.

Of the many commercial cultivars known to the present inventor, the most similar in comparison to 'Fisrocco' is the variety 'Fisam'. In comparison to 'Fisam', 'Fisrocco' has similarly shaped flowers with similar kind of markings on petals, but with a more pinkish hue of flower color, somewhat umbels, and foliage with a more glossy surface, and slightly taller plant habit.

BRIEF DESCRIPTION OF THE DRAWING

The accompanying photographic drawing shows typical flower and foliage characteristics of 'Fisrocco'. with colors being as true as possible with an illustration of this type. The measurements were taken in Langley, British Columbia, Canada, on Jul. 20, 2000. The plants were growing in 6 inch pots in a greenhouse, and had 15 weeks of cultivation time from planting of rooted cuttings on Apr. 3, 2000. The plants had not been pinched.

In the following description color references are made to The Royal Horticultural Society Colour Chart (R.H.S.). The color values were determined indoors from plants developed in a green-house in May, 2000, in Hillscheid, Germany.

CLASSIFICATION

Botanical: A hybrid of the species *Pelargonium peltatum* L'Hérit.

Commercial: Ivy-leafed geranium, cv. 'Fisrocco'.

INFLORESCENCE

Umbel:

*Shape.*—Almost semi-spherical, slightly irregular.

*Average diameter.*—92 mm.

*Average depth.*—48 mm.

*Peduncle length.*—142 mm.

*Peduncle color.*—Light green, RHS 143B.

*Pedicel.*—31 mm longwith spur.

*Pedicel color, middle part.*—Mainly green, RHS 143B, with a reddish line/streak RHS 179A on one side of the upper part.

*Number of flowers per umbel.*—9–14.

*Lastingness of umbel.*—Approximately 15 days at 18° C.

Corolla:

*Average diameter.*—52 mm.

*Form.*—Semi-double to double.

*Shape.*—Round outline, but with a narrow gap between upper and lower petals.

*Number of petals.*—11–13.

*Petal size.*—Upper petals are 29–31 mm in length, 20–22 in diameter; lower petals are 25 mm in length, 16–18 mm in diameter; inner petals are smaller.

*Petal shape.*—Obovate, upper end is rounded, attenuate base, margin entire.

*Color (general tonality from a distance of three meters)* .—Intense purple-pink.

*Color of upper petals.*—RHS 80 C.

*Markings of upper petals.*—Relatively strong, two violet veins RHS 74B, and a dark-red macule RHS 187C.

*Color of lower petals.*—RHS 80 C.

*Markings of lower petals.*—Fine reddish lines or a tiny red dot may occur, color varying between RHS 57 B and RHS 57 C.

*Color of lower surface of petals.*—RHS 75 A to 75 B, in parts a more pinkish hue, with strong violet-red veins RHS 74 B at the under side of the upper petals.

*Color of sepals.*—Outer surface green, RHS 143 A, inner surface light green RHS 143 C, occassionally slight infusion of anthocyanin RHS 179 A may occur on the largest sepal's outer surface, inner surface RHS 179 B.

Number of sepals.—5.

Sepal size.—13–15 mm in length, 4–5 in diameter for upper sepal; 2.5–3.5 mm in diameter for other sepals.

*Sepal shape.*—Linear to lanceolate, truncate base, acute tip, margin entire.

Bud: (just prior to petals unfolding):

*Shape.*—Wide elliptic.

*Bud color.*—Between RHS 74 C and RHS 74 D.

*Sepal color (lower part).*—Light green, RHS 143 B.

*Petal color (upper part).*—Purple-pink, vary between RHS 74 C and RHS 74D.

*Length.*—18 mm.

*Width.*—12 mm.

Reproductive organs:

*Androecium.*—3–5 fertile anthers or petaloids, with whitish to pink filaments and orange pollen, RHS 33A, moderate pollen production.

*Gynoecium.*—Whitish style, purple-pink stigma, one pistil per flower.

*Fertility/seed set.*—No seed set observed.

Spring flowering response period: In Hillscheid, Germany, in 2000, plants had on average 0.6 flowers opened 12 weeks after planting of rooted cuttings (pinched plants).

Outdoor flower production: Floriferous, numberous, medium sized inflorescences, flower count in Hillscheid, Germany, indicated about 5.0 inflorescences per plant for mid May, 2000.

Durability: Good shatter resistance, average rain resistance, flower color somewhat susceptible to fading.

Lastingness of the individual bloom: Approximately 9 days at 18° C.

Fragrance: None.

PLANT

Foliage:

*Shape.*—Ivy-shaped with weak lobes, and with closed base, lowest lobes forming a cordate shape.

*Margin.*—Entire.

*Size of leaf.*—79 mm wide and 33–38 mm long.

*Color of upper surface.*—Light medium green, vary between RHS 137 D and RHS 143 A.

*Color of lower surface.*—RHS 137 D.

*Zonation.*—Brown, approximately RHS 166 A, distinctness is medium.

*Petioles.*—40–50 mm long, 2–3 mm diameter, dull green color approximately RHS 137D.

General appearance and form:

*Stem color.*—Light green, RHS 137 D.

*Internode length.*—25–35 mm.

*Branching pattern.*—5.0 branches.

*Plant height.*—42 cm as measured from the top of the soil (from the base of the main stem) to the tops of the branches (15 week old plants in Langley, Canada), 70–80 cm (in mid September in Hillscheid, Germany 31 weeks old).

Disease pest resistance susceptibility: None observed to date.

I claim:

1. A new and distinct cultivar of geranium plant named 'Fisrocco', as described and illustrated.

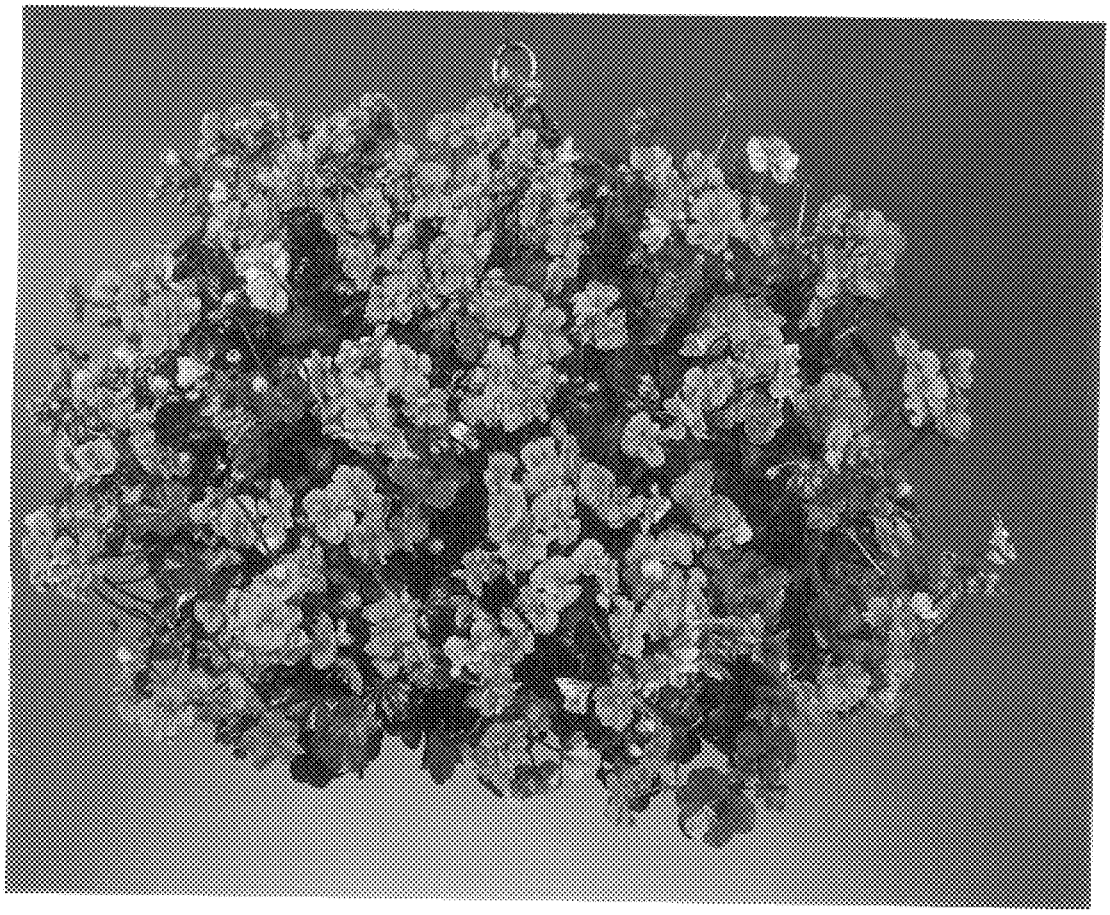

* * * * *